United States Patent [19]
Ueki et al.

[11] Patent Number: 5,973,226
[45] Date of Patent: Oct. 26, 1999

[54] METHOD OF CHANGING THE COMPOSITION OF THE PHOSPHOLIPID PRODUCED BY THE LIVING BODY AND RECOMBINANT VECTOR THEREFOR

[75] Inventors: Jun Ueki, Iwata-gun; Shinji Morioka, Tokyo, both of Japan

[73] Assignee: Japan Tobacco Inc., Tokyo, Japan

[21] Appl. No.: 08/945,024

[22] PCT Filed: Feb. 20, 1997

[86] PCT No.: PCT/JP97/00466

§ 371 Date: Oct. 21, 1997

§ 102(e) Date: Oct. 21, 1997

[87] PCT Pub. No.: WO97/31106

PCT Pub. Date: Aug. 28, 1997

[30] Foreign Application Priority Data

Feb. 21, 1996 [JP] Japan ................... 8-058320

[51] Int. Cl.⁶ .................. C12N 15/82; C12N 15/84; C12N 5/04; C12N 15/29
[52] U.S. Cl. .................. 800/285; 536/23.6; 536/24.5; 536/23.1; 435/69.1; 435/468; 435/410; 435/418; 435/419; 435/320.1; 800/278; 800/295; 800/281; 800/320.2
[58] Field of Search .................. 536/23.6, 24.5, 536/23.1; 435/419, 69.1, 468, 410, 418, 320.1; 800/205, DIG. 57, DIG. 52, DIG. 9, 278, 285, 295, 281, 320.2

[56] References Cited

U.S. PATENT DOCUMENTS 4,801,540  1/1989  Hiatt et al. .
5,107,065  4/1992  Shewmaker et al. .
5,453,566  9/1995  Shewmaker et al. .

FOREIGN PATENT DOCUMENTS 0685559  12/1995  European Pat. Off. .
9630510  10/1996  WIPO .

OTHER PUBLICATIONS

Ueki et al., Plant Cell Physiol. 36(5): 903–914 (1995).

Naploi et al. 1989. The Plant Cell. vol. 2: 278–289.

Carvalho et al. The EMBO Journal. vol. 11: 5995–5602, 1992.

Wan and Lemaux. Plant Physiology. 1994. vol. 104: 37–48.

Zaghmout and Torello. 1992. vol. 140: 101–105.

Chan et al. Plant Molecular Biology. 1993. vol. 22: 491–506.

Tsang et al. FASEB Journal. 1992. vol. 6: 1922.

*Primary Examiner*—Lynette R. F. Smith
*Assistant Examiner*—Ousama Zaghmout
*Attorney, Agent, or Firm*—Birch, Stewart, Kolasch & Birch, LLP

[57] ABSTRACT

A method for artificially changing the composition of phospholipids produced by cells is disclosed. According to the method of the invention, the host cell is transformed with a recombinant DNA having an antisense gene of phospholipase D gene, which antisense gene is expressed in the host cell to produce a mRNA that hybridizes with mRNA of phospholipase D gene in the host cell thereby inhibiting expression of the phospholipase D gene.

5 Claims, No Drawings

5,973,226

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3040 base pairs
      (B) TYPE: nucleic acid
      (C) STRANDEDNESS: double
      (D) TOPOLOGY: linear (ii) MOLECULE TYPE: cDNA to mRNA (ix) FEATURE:
      (A) NAME/KEY: CDS
      (B) LOCATION: 182..2617

(xi) SEQUENCE DESCRIPTION: SEQ ID NO:1:

```
AGTCTCTCTT CTCCCGCAAT TTTATAATCT CGATCGATCC AATCTGCTCC CCTTCTTCTT      60

CTACTCTCCC CATCTCGGCT CTCGCCATCG CCATCCTCCT CTCCCTTCCC GGAGAAGACG     120

CCTCCCTCCG CCGATCACCA CCCGGTAGGG CGAGGAGGGA GCCAAATCCA AATCAGCAGC     180

C ATG GCG CAG ATG CTG CTC CAT GGG ACG CTG CAC GCC ACC ATC TTC         226
  Met Ala Gln Met Leu Leu His Gly Thr Leu His Ala Thr Ile Phe
  1               5                   10                  15

GAG GCG GCG TCG CTC TCC AAC CCG CAC CGC GCC AGC GGA AGC GCC CCC       274
Glu Ala Ala Ser Leu Ser Asn Pro His Arg Ala Ser Gly Ser Ala Pro
                20                  25                  30

AAG TTC ATC CGC AAG TTT GTG GAG GGG ATT GAG GAC ACT GTG GGT GTC       322
Lys Phe Ile Arg Lys Phe Val Glu Gly Ile Glu Asp Thr Val Gly Val
            35                  40                  45

GGC AAA GGC GCC ACC AAG GTG TAT TCT ACC ATT GAT CTG GAG AAA GCT       370
Gly Lys Gly Ala Thr Lys Val Tyr Ser Thr Ile Asp Leu Glu Lys Ala
        50                  55                  60

CGT GTA GGG CGA ACT AGG ATG ATA ACC AAT GAG CCC ATC AAC CCT CGC       418
Arg Val Gly Arg Thr Arg Met Ile Thr Asn Glu Pro Ile Asn Pro Arg
    65                  70                  75

TGG TAT GAG TCG TTC CAC ATC TAT TGC GCT CAT ATG GCT TCC AAT GTG       466
Trp Tyr Glu Ser Phe His Ile Tyr Cys Ala His Met Ala Ser Asn Val
80                  85                  90                  95

ATC TTC ACT GTC AAG ATT GAT AAC CCT ATT GGG GCA ACG AAT ATT GGG       514
Ile Phe Thr Val Lys Ile Asp Asn Pro Ile Gly Ala Thr Asn Ile Gly
                100                 105                 110

AGG GCT TAC CTG CCT GTC CAA GAG CTT CTC AAT GGA GAG GAG ATT GAC       562
Arg Ala Tyr Leu Pro Val Gln Glu Leu Leu Asn Gly Glu Glu Ile Asp
            115                 120                 125

AGA TGG CTC GAT ATC TGT GAT AAT AAC CGC GAG TCT GTT GGT GAG AGC       610
Arg Trp Leu Asp Ile Cys Asp Asn Asn Arg Glu Ser Val Gly Glu Ser
        130                 135                 140

AAG ATC CAT GTG AAG CTT CAG TAC TTC GAT GTT TCC AAG GAT CGC AAT       658
Lys Ile His Val Lys Leu Gln Tyr Phe Asp Val Ser Lys Asp Arg Asn
    145                 150                 155

TGG GCG AGG GGT GTC CGC AGT ACC AAG TAT CCA GGT GTT CCT TAC ACC       706
Trp Ala Arg Gly Val Arg Ser Thr Lys Tyr Pro Gly Val Pro Tyr Thr
160                 165                 170                 175

TTC TTC TCT CAG AGG CAA GGG TGC AAA GTT ACC TTG TAC CAA GAT GCT       754
Phe Phe Ser Gln Arg Gln Gly Cys Lys Val Thr Leu Tyr Gln Asp Ala
                180                 185                 190

CAT GTC CCA GAC AAC TTC ATT CCA AAG ATT CCG CTT GCC GAT GGC AAG       802
His Val Pro Asp Asn Phe Ile Pro Lys Ile Pro Leu Ala Asp Gly Lys
            195                 200                 205

AAT TAT GAA CCC CAC AGA TGC TGG GAG GAT ATC TTT GAT GCT ATA AGC       850
Asn Tyr Glu Pro His Arg Cys Trp Glu Asp Ile Phe Asp Ala Ile Ser
        210                 215                 220

AAT GCT CAA CAT TTG ATT TAC ATC ACT GGC TGG TCT GTA TAC ACT GAG       898
Asn Ala Gln His Leu Ile Tyr Ile Thr Gly Trp Ser Val Tyr Thr Glu
    225                 230                 235

ATC ACC TTG GTT AGG GAC TCC AAT CGT CCA AAA CCT GGA GGG GAT GTC       946
Ile Thr Leu Val Arg Asp Ser Asn Arg Pro Lys Pro Gly Gly Asp Val
240                 245                 250                 255

ACC CTT GGG GAG TTG CTC AAG AAG AAG GCC AGT GAA GGT GTT CGG GTC       994
Thr Leu Gly Glu Leu Leu Lys Lys Lys Ala Ser Glu Gly Val Arg Val
                260                 265                 270

CTC ATG CTT GTG TGG GAT GAC AGG ACT TCA GTT GGT TTG CTA AAG AGG      1042
Leu Met Leu Val Trp Asp Asp Arg Thr Ser Val Gly Leu Leu Lys Arg
            275                 280                 285
```

-continued

```
GAT GGC TTG ATG GCA ACA CAT GAT GAG GAA ACT GAA AAT TAC TTC CAT        1090
Asp Gly Leu Met Ala Thr His Asp Glu Glu Thr Glu Asn Tyr Phe His
        290                 295                 300

GGC TCT GAC GTG AAC TGT GTT CTA TGC CCT CGC AAC CCT GAT GAC TCA        1138
Gly Ser Asp Val Asn Cys Val Leu Cys Pro Arg Asn Pro Asp Asp Ser
305                 310                 315

GGC AGC ATT GTT CAG GAT CTG TCG ATC TCA ACT ATG TTT ACA CAC CAT        1186
Gly Ser Ile Val Gln Asp Leu Ser Ile Ser Thr Met Phe Thr His His
320                 325                 330                 335

CAG AAG ATA GTA GTT GAC CAT GAG TTG CCA AAC CAG GGC TCC CAA            1234
Gln Lys Ile Val Val Asp His Glu Leu Pro Asn Gln Gly Ser Gln
            340                 345                 350

CAA AGG AGG ATA GTC AGT TTC GTT GGT GGC CTT GAT CTC TGT GAT GGA        1282
Gln Arg Arg Ile Val Ser Phe Val Gly Gly Leu Asp Leu Cys Asp Gly
                355                 360                 365

AGG TAT GAC ACT CAG TAC CAT TCT TTG TTT AGG ACA CTC GAC AGT ACC        1330
Arg Tyr Asp Thr Gln Tyr His Ser Leu Phe Arg Thr Leu Asp Ser Thr
        370                 375                 380

CAT CAT GAT GAC TTC CAC CAG CCA AAC TTT GCC ACT GCA TCA ATC AAA        1378
His His Asp Asp Phe His Gln Pro Asn Phe Ala Thr Ala Ser Ile Lys
            385                 390                 395

AAG GGT GGA CCT AGA GAG CCA TGG CAT GAT ATT CAC TCA CGG CTG GAA        1426
Lys Gly Gly Pro Arg Glu Pro Trp His Asp Ile His Ser Arg Leu Glu
400                 405                 410                 415

GGG CCA ATC GCA TGG GAT GTT CTT TAC AAT TTC GAG CAG AGA TGG AGA        1474
Gly Pro Ile Ala Trp Asp Val Leu Tyr Asn Phe Glu Gln Arg Trp Arg
                420                 425                 430

AAG CAG GGT GGT AAG GAT CTC CTT CTG CAG CTC AGG GAT CTG TCT GAC        1522
Lys Gln Gly Gly Lys Asp Leu Leu Leu Gln Leu Arg Asp Leu Ser Asp
            435                 440                 445

ACT ATT ATT CCA CCT TCT CCT GTT ATG TTT CCA GAG GAC AGA GAA ACA        1570
Thr Ile Ile Pro Pro Ser Pro Val Met Phe Pro Glu Asp Arg Glu Thr
        450                 455                 460

TGG AAT GTT CAG CTA TTT AGA TCC ATT GAT GGT GGT GCT GCT TTT GGG        1618
Trp Asn Val Gln Leu Phe Arg Ser Ile Asp Gly Gly Ala Ala Phe Gly
            465                 470                 475

TTC CCT GAT ACC CCT GAG GAG GCT GCA AAA GCT GGG CTT GTA AGC GGA        1666
Phe Pro Asp Thr Pro Glu Glu Ala Ala Lys Ala Gly Leu Val Ser Gly
480                 485                 490                 495

AAG GAT CAA ATC ATT GAC AGG AGC ATC CAG GAT GCA TAC ATA CAT GCC        1714
Lys Asp Gln Ile Ile Asp Arg Ser Ile Gln Asp Ala Tyr Ile His Ala
                500                 505                 510

ATC CGG AGG GCA AAG AAC TTC ATC TAT ATA GAG AAC CAA TAC TTC CTT        1762
Ile Arg Arg Ala Lys Asn Phe Ile Tyr Ile Glu Asn Gln Tyr Phe Leu
            515                 520                 525

GGA AGT TCC TAT GCC TGG AAA CCC GAG GGC ATC AAG CCT GAA GAC ATT        1810
Gly Ser Ser Tyr Ala Trp Lys Pro Glu Gly Ile Lys Pro Glu Asp Ile
        530                 535                 540

GGT GCC CTG CAT TTG ATT CCT AAG GAG CTT GCA CTG AAA GTT GTC AGT        1858
Gly Ala Leu His Leu Ile Pro Lys Glu Leu Ala Leu Lys Val Val Ser
545                 550                 555

AAG ATT GAA GCC GGG GAA CGG TTC ACT GTT TAT GTT GTG GTG CCA ATG        1906
Lys Ile Glu Ala Gly Glu Arg Phe Thr Val Tyr Val Val Val Pro Met
560                 565                 570                 575

TGG CCT GAG GGT GTT CCA GAG AGT GGA TCT GTT CAG GCA ATC CTG GAC        1954
Trp Pro Glu Gly Val Pro Glu Ser Gly Ser Val Gln Ala Ile Leu Asp
                580                 585                 590

TGG CAA AGG AGA ACA ATG GAG ATG ATG TAC ACT GAC ATT ACA GAG GCT        2002
Trp Gln Arg Arg Thr Met Glu Met Met Tyr Thr Asp Ile Thr Glu Ala
            595                 600                 605
```

-continued

| | | |
|---|---|---|
| CTC CAA GCC AAG GGA ATT GAA GCG AAC CCC AAG GAC TAC CTC ACT TTC<br>Leu Gln Ala Lys Gly Ile Glu Ala Asn Pro Lys Asp Tyr Leu Thr Phe<br>610              615                       620 | 2050 |
| TTC TGC TTG GGT AAC CGT GAG GTG AAG CAG GCT GGG GAA TAT CAG CCT<br>Phe Cys Leu Gly Asn Arg Glu Val Lys Gln Ala Gly Glu Tyr Gln Pro<br>625              630              635 | 2098 |
| GAA GAA CAA CCA GAA GCT GAC ACT GAT TAC AGC CGA GCT CAG GAA GCT<br>Glu Glu Gln Pro Glu Ala Asp Thr Asp Tyr Ser Arg Ala Gln Glu Ala<br>640              645                  650             655 | 2146 |
| AGG AGG TTC ATG ATC TAT GTC CAC ACC AAA ATG ATG ATA GTT GAC GAT<br>Arg Arg Phe Met Ile Tyr Val His Thr Lys Met Met Ile Val Asp Asp<br>              660                     665                   670 | 2194 |
| GAG TAC ATC ATC ATC GGT TCT GCA AAC ATC AAC CAG AGG TCG ATG GAC<br>Glu Tyr Ile Ile Ile Gly Ser Ala Asn Ile Asn Gln Arg Ser Met Asp<br>              675                     680                   685 | 2242 |
| GGC GCT AGG GAC TCT GAG ATC GCC ATG GGC GGG TAC CAG CCA TAC CAT<br>Gly Ala Arg Asp Ser Glu Ile Ala Met Gly Gly Tyr Gln Pro Tyr His<br>         690                     695                   700 | 2290 |
| CTG GCG ACC AGG CAA CCA GCC CGT GGC CAG ATC CAT GGC TTC CGG ATG<br>Leu Ala Thr Arg Gln Pro Ala Arg Gly Gln Ile His Gly Phe Arg Met<br>705              710                       715 | 2338 |
| GCG CTG TGG TAC GAG CAC CTG GGA ATG CTG GAT GAT GTG TTC CAG CGC<br>Ala Leu Trp Tyr Glu His Leu Gly Met Leu Asp Asp Val Phe Gln Arg<br>720              725                     730             735 | 2386 |
| CCC GAG AGC CTG GAG TGT GTG CAG AAG GTG AAC AGG ATC GCG GAG AAG<br>Pro Glu Ser Leu Glu Cys Val Gln Lys Val Asn Arg Ile Ala Glu Lys<br>              740                     745                   750 | 2434 |
| TAC TGG GAC ATG TAC TCC AGC GAC GAC CTC CAG CAG GAC CTC CCT GGC<br>Tyr Trp Asp Met Tyr Ser Ser Asp Asp Leu Gln Gln Asp Leu Pro Gly<br>         755                     760                   765 | 2482 |
| CAC CTC CTC AGC TAC CCC ATT GGC GTC GCC AGC GAT GGT GTG GTG ACT<br>His Leu Leu Ser Tyr Pro Ile Gly Val Ala Ser Asp Gly Val Val Thr<br>         770                     775                   780 | 2530 |
| GAG CTG CCC GGG ATG GAG TAC TTT CCT GAC ACA CGG GCC CGC GTC CTC<br>Glu Leu Pro Gly Met Glu Tyr Phe Pro Asp Thr Arg Ala Arg Val Leu<br>785              790                     795 | 2578 |
| GGC GCC AAG TCG GAT TAC ATG CCC CCC ATC CTC ACC TCA TAGACGAGGA<br>Gly Ala Lys Ser Asp Tyr Met Pro Pro Ile Leu Thr Ser<br>800                     805                     810 | 2627 |
| AGCACTACAC TACAATCTGC TGGCTTCTCC TGTCAGTCCT TCTGTACTTC TTCAGTTTGG | 2687 |
| TGGCGAGATG GTATGGCCGT TGTTCAGAAT TTCTTCAGAA TAGCAGTTGT TACAGTTGTG | 2747 |
| AATCATAAAG TAATAAGTGC AGTATCTGTG CATGGTTGAG TTGGGAAGAA GATCGGGGAT | 2807 |
| GCAATGATGC TTGTGAAGTT GTGATGCCGT TTGTAAGATG GGAAGTTGGG AACTACTAAG | 2867 |
| TAATTGGCAT GATTGTACTT TGCACTACTG TTTAGCGTTG TTGATACTGG TTAACCGTGT | 2927 |
| GTTCATCTGA ACTTGATTCT TGATGCAGTT TGTGGCATTA CCAGTTTATC ATCGTTCTTC | 2987 |
| AGGAAAAAAA AAAAAAAAA AAAAAAAAAA AAAAAAAAA AAAAAAAAAA AAA | 3040 |

(2) INFORMATION FOR SEQ ID NO:2:

(i) SEQUENCE CHARACTERISTICS:
        (A) LENGTH: 812 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Gln Met Leu Leu His Gly Thr Leu His Ala Thr Ile Phe Glu
1              5                    10                  15

-continued

```
Ala Ala Ser Leu Ser Asn Pro His Arg Ala Ser Gly Ser Ala Pro Lys
            20                  25                  30
Phe Ile Arg Lys Phe Val Glu Gly Ile Glu Asp Thr Val Gly Val Gly
        35                  40                  45
Lys Gly Ala Thr Lys Val Tyr Ser Thr Ile Asp Leu Glu Lys Ala Arg
 50                  55                  60
Val Gly Arg Thr Arg Met Ile Thr Asn Glu Pro Ile Asn Pro Arg Trp
 65                  70                  75                  80
Tyr Glu Ser Phe His Ile Tyr Cys Ala His Met Ala Ser Asn Val Ile
                85                  90                  95
Phe Thr Val Lys Ile Asp Asn Pro Ile Gly Ala Thr Asn Ile Gly Arg
            100                 105                 110
Ala Tyr Leu Pro Val Gln Glu Leu Leu Asn Gly Glu Ile Asp Arg
        115                 120                 125
Trp Leu Asp Ile Cys Asp Asn Asn Arg Glu Ser Val Gly Glu Ser Lys
        130                 135                 140
Ile His Val Lys Leu Gln Tyr Phe Asp Val Ser Lys Asp Arg Asn Trp
145                 150                 155                 160
Ala Arg Gly Val Arg Ser Thr Lys Tyr Pro Gly Val Pro Tyr Thr Phe
                165                 170                 175
Phe Ser Gln Arg Gln Gly Cys Lys Val Thr Leu Tyr Gln Asp Ala His
            180                 185                 190
Val Pro Asp Asn Phe Ile Pro Lys Ile Pro Leu Ala Asp Gly Lys Asn
        195                 200                 205
Tyr Glu Pro His Arg Cys Trp Glu Asp Ile Phe Asp Ala Ile Ser Asn
        210                 215                 220
Ala Gln His Leu Ile Tyr Ile Thr Gly Trp Ser Val Tyr Thr Glu Ile
225                 230                 235                 240
Thr Leu Val Arg Asp Ser Asn Arg Pro Lys Pro Gly Gly Asp Val Thr
                245                 250                 255
Leu Gly Glu Leu Leu Lys Lys Lys Ala Ser Glu Gly Val Arg Val Leu
            260                 265                 270
Met Leu Val Trp Asp Asp Arg Thr Ser Val Gly Leu Leu Lys Arg Asp
        275                 280                 285
Gly Leu Met Ala Thr His Asp Glu Glu Thr Glu Asn Tyr Phe His Gly
        290                 295                 300
Ser Asp Val Asn Cys Val Leu Cys Pro Arg Asn Pro Asp Asp Ser Gly
305                 310                 315                 320
Ser Ile Val Gln Asp Leu Ser Ile Ser Thr Met Phe Thr His His Gln
                325                 330                 335
Lys Ile Val Val Asp His Glu Leu Pro Asn Gln Gly Ser Gln Gln
            340                 345                 350
Arg Arg Ile Val Ser Phe Val Gly Gly Leu Asp Leu Cys Asp Gly Arg
        355                 360                 365
Tyr Asp Thr Gln Tyr His Ser Leu Phe Arg Thr Leu Asp Ser Thr His
        370                 375                 380
His Asp Asp Phe His Gln Pro Asn Phe Ala Thr Ala Ser Ile Lys Lys
385                 390                 395                 400
Gly Gly Pro Arg Glu Pro Trp His Asp Ile His Ser Arg Leu Glu Gly
                405                 410                 415
Pro Ile Ala Trp Asp Val Leu Tyr Asn Phe Glu Gln Arg Trp Arg Lys
            420                 425                 430
```

-continued

```
Gln Gly Gly Lys Asp Leu Leu Leu Gln Leu Arg Asp Leu Ser Asp Thr
            435                 440                 445

Ile Ile Pro Pro Ser Pro Val Met Phe Pro Glu Asp Arg Glu Thr Trp
450                 455                 460

Asn Val Gln Leu Phe Arg Ser Ile Asp Gly Ala Ala Phe Gly Phe
465                 470                 475                 480

Pro Asp Thr Pro Glu Glu Ala Ala Lys Ala Gly Leu Val Ser Gly Lys
                485                 490                 495

Asp Gln Ile Ile Asp Arg Ser Ile Gln Asp Ala Tyr Ile His Ala Ile
                500                 505                 510

Arg Arg Ala Lys Asn Phe Ile Tyr Ile Glu Asn Gln Tyr Phe Leu Gly
            515                 520                 525

Ser Ser Tyr Ala Trp Lys Pro Glu Gly Ile Lys Pro Glu Asp Ile Gly
530                 535                 540

Ala Leu His Leu Ile Pro Lys Glu Leu Ala Leu Lys Val Val Ser Lys
545                 550                 555                 560

Ile Glu Ala Gly Glu Arg Phe Thr Val Tyr Val Val Pro Met Trp
                565                 570                 575

Pro Glu Gly Val Pro Glu Ser Gly Ser Val Gln Ala Ile Leu Asp Trp
                580                 585                 590

Gln Arg Arg Thr Met Glu Met Met Tyr Thr Asp Ile Thr Glu Ala Leu
            595                 600                 605

Gln Ala Lys Gly Ile Glu Ala Asn Pro Lys Asp Tyr Leu Thr Phe Phe
610                 615                 620

Cys Leu Gly Asn Arg Glu Val Lys Gln Ala Gly Glu Tyr Gln Pro Glu
625                 630                 635                 640

Glu Gln Pro Glu Ala Asp Thr Asp Tyr Ser Arg Ala Gln Glu Ala Arg
                645                 650                 655

Arg Phe Met Ile Tyr Val His Thr Lys Met Met Ile Val Asp Asp Glu
                660                 665                 670

Tyr Ile Ile Ile Gly Ser Ala Asn Ile Asn Gln Arg Ser Met Asp Gly
            675                 680                 685

Ala Arg Asp Ser Glu Ile Ala Met Gly Gly Tyr Gln Pro Tyr His Leu
690                 695                 700

Ala Thr Arg Gln Pro Ala Arg Gly Gln Ile His Gly Phe Arg Met Ala
705                 710                 715                 720

Leu Trp Tyr Glu His Leu Gly Met Leu Asp Asp Val Phe Gln Arg Pro
                725                 730                 735

Glu Ser Leu Glu Cys Val Gln Lys Val Asn Arg Ile Ala Glu Lys Tyr
                740                 745                 750

Trp Asp Met Tyr Ser Ser Asp Leu Gln Gln Asp Leu Pro Gly His
            755                 760                 765

Leu Leu Ser Tyr Pro Ile Gly Val Ala Ser Asp Gly Val Val Thr Glu
770                 775                 780

Leu Pro Gly Met Glu Tyr Phe Pro Asp Thr Arg Ala Arg Val Leu Gly
785                 790                 795                 800

Ala Lys Ser Asp Tyr Met Pro Pro Ile Leu Thr Ser
                805                 810
```

(2) INFORMATION FOR SEQ ID NO:3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "PRIMER"

(xi) SEQUENCE DESCRIPTION: SEQ ID NO:3:

GCAGGAGCTC TAGAGGGATG ACAGGACTTC AGTTGGT                                    37

(2) INFORMATION FOR SEQ ID NO:4:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid
             (A) DESCRIPTION: /desc = "PRIMER"

(xi) SEQUENCE DESCRIPTION: SEQ ID NO:4:

GGGAATTCGG ATCCGCTTCT GGTTGTTCTT CAGGC                                      35
```

METHOD OF CHANGING THE COMPOSITION OF THE PHOSPHOLIPID PRODUCED BY THE LIVING BODY AND RECOMBINANT VECTOR THEREFOR

TECHNICAL FIELD

The present invention relates to a method for changing the composition of phospholipids produced by an organism and to a recombinant vector therefor.

BACKGROUND ART

Phospholipids are naturally occurring nonionic surface active agents which are valuable in the field of foods, medicines and production of various materials. Phospholipids are mainly produced from biological materials, and the composition of the phospholipids is one of the elements which determine the quality of the material.

The factor which participates in the determination of the composition of phospholipids is unknown and no methods by which the composition of phospholipids is changed by genetic engineering process have been reported.

DISCLOSURE OF THE INVENTION

An object of the present invention is to provide a method for artificially changing the composition of phospholipids produced by cells.

The present inventors intensively studied to discover that the composition of phospholipids produced by cells can be changed by inhibiting expression of the gene encoding phospholipase D (hereinafter also referred to as "PLD") which is a kind of phospholipase, thereby completing the present invention.

That is, the present invention provides a method for changing the composition of phospholipids produced by a host cell, comprising transforming said host cell with a recombinant DNA having an antisense gene of a phospholipase D gene, which antisense gene is expressed in said host cell to produce an mRNA that hybridizes with mRNA of a phospholipase D gene in said host cell thereby inhibiting expression of said phospholipase D gene. The present invention also provides a recombinant DNA having an antisense gene of a phospholipase D gene, which antisense gene is expressed in a host cell to produce an mRNA that hybridizes with mRNA of phospholipase D gene in said host cell thereby inhibiting expression of said phospholipase D gene.

BEST MODE FOR CARRYING OUT THE INVENTION

PLD is a kind of phospholipase, which, for example, catalyzes the reaction of hydrolyzing lecithin to liberate phosphatidic acid and choline. This enzyme is known to occur in plants, animals and microorganisms. The host cell employed in the method of the present invention may be any cell of plants, animals and microorganisms, as long as it has a PLD gene. The host cell is preferably a plant cell, more preferably a cell of a spermatophyte.

The term "spermatophyte" herein means plants which flower and form seeds. In the present invention, among the cells of spermatophytes, cells of monocotyledons, especially rice, are preferred.

The recombinant vector used for the method of the present invention comprises an antisense gene of the PLD gene, which antisense gene can inhibit expression of the PLD gene in the host cells. The nucleotide sequences of PLD genes are known. For example, the nucleotide sequences of PLD genes of microorganisms and animals are described in Japanese Laid-open Patent Application (Kokai) No. 3-187382; Adrian L. M. Hodgson, Phllip Bird, and Ian T. Nisbet 1990, "Cloning, nucleotide sequence, and expression in *Escherichia coli* of the Phospholipase D gene from Corynebacterium pseudotuberculosis" Journal of Bacteriology 172, 1256–1261; and Japanese Laid-open Patent Application (Kokai) No. 5-76357. As for PLD genes of plants, the nucleotide sequences of the PLD genes of rice and maize are described in WO95/09234. Further, PLD genes originated from Arabidopsis and castor bean have also been reported (Plant Physiol.(1995)109:1497–1499, Plant Gene Register PGR95-096, J. Biol. Chem. (1994) 269:20312–20317).

In the above-mentioned reference (Plant Gene Register PGR95-096), it is described that PLD genes originated from rice, maize, Arabidopsis and castor bean have high homologies each other, so that it is suggested that PLD genes of spermatophytes are well conserved. Therefore, PLD genes of spermatophytes may easily be obtained by a conventional method using the above-mentioned sequences of the PLD genes of rice, maize and the like as probes.

Thus, since the nucleotide sequences of PLD genes are known, antisense genes which yield mRNAs complementary to at least a region of the mRNAs produced using the PLD genes as templates may easily be prepared. That is, the antisense gene of a PLD gene is a double-stranded DNA having the same sequence as the entire or a part of the PLD gene, which is to be inserted in the direction in which the sense chain of the PLD gene serves as the antisense chain (this is hereinafter also referred to as "insert in the antisense direction"). The length of the antisense gene is not necessarily the entire length of the PLD gene but may be a length at which expression of the PLD gene is inhibited. That is, the length of the antisense gene is preferably not less than 300 bp and not more than the entire length, more preferably not less than 1 kbp and not more than the entire length of the PLD gene.

Since the nucleotide sequences of the PLD genes are known, the antisense genes of the PLD genes may easily be prepared by chemical synthesis, by PCR using the PLD genes as templates or by RT-PCR using the cDNAs of the PLD genes as templates.

In the present invention, the antisense gene to be introduced is not restricted as long as the antisense gene encodes a mRNA which hybridizes in vivo with the mRNA of the PLD gene in the host cell. The homology between the complementary chain of the mRNA produced by the antisense gene and the mRNA of the PLD gene in the host is preferably not less than 70%, more preferably not less than 80%, still more preferably not less than 90%, still more preferably not less than 95%, and most preferably 100% (i.e., the antisense gene of the PLD gene in the host cell).

The recombinant vector used in the method of the present invention is one which can express the above-mentioned antisense gene of the PLD gene in the host cells. Therefore, the recombinant vector has a replication origin effective in the host cells and a promoter, and the antisense gene is inserted downstream of the promoter. The recombinant vector may preferably have a terminator and a selection marker such as a drug resistant gene. A number of such expression vectors are known for various host cells and commercially available. Since commercially available expression vectors have a region called multicloning site having a number of restriction sites downstream of the promoter, the recombinant vector according to the present invention may easily be prepared by inserting the above-mentioned antisense gene into the multicloning site.

The host cells are then transformed with the recombinant vector prepared as described above. Transformation may be carried out by the methods well-known for each type of the host cells. For example, in the Examples described below, the well-known electroporation method is employed for transforming rice cells. Needless to say, however, the method of transformation is not restricted to the electroporation method.

The transformed cells are then selected. The selection may be carried out based on the selection marker in the expression vector. Further, it is more reliable to confirm that the antisense gene does exist in the cell containing the selection marker by Southern analysis or the like.

Phospholipids are then recovered from the transformed cells. Extraction of the phospholipids may be carried out by conventional methods. For example, phospholipids may be extracted by treating the cells in boiling water and then extracting the resultant with an organic solvent. In cases where the host cells are the plant cells such as rice cells, which can regenerate a plant from a callus, the transformation treatment may be performed on protoplasts, plants may be regenerated by culturing the callus, and phospholipids may be recovered from the regenerated plants. This method is more suited for large scale production. In this case, it is preferred to confirm existence of the antisense gene by Southern analysis in the regenerated plants.

Phospholipid molecules are composed of phosphatidyl choline (hereinafter also referred to as "PC"), phosphatidyl serine (hereinafter also referred to as "PS"), phosphatidyl ethanolamine (hereinafter also referred to as "PE"), and the like, and the composition of the phospholipids is determined by the ratio of amounts of these components. The method of the present invention is to change the ratio of the amounts of all of the components constituting the phospholipids and not to change the content of a particular phospholipid. Therefore, although only the ratios of amounts of PE an PS are measured in the Examples described below, the change of the composition of the phospholipids is not restricted thereto.

By the present invention, changing the composition of phospholipids produced by organisms by a genetic engineering process was first attained. Therefore, the present invention enables to produce phospholipids which have higher utility values than the naturally occurring phospholipids in the field of foods, medicines and production of various materials.

That is, concrete effects of the present invention may include the following:
1. PC which is the main component of the phospholipids is used as digestible surfactant, food additive such as emulsifier and as wrapping membrane of drugs. By changing the composition of the phospholipids, for example, the following effects may be obtained.

By increasing the PC content, the PC may be purified very easily.

By increasing the contents of phospholipids other than PC, these phospholipids may be purified easily, so that it is expected that surfactants, emulsifiers and the like having new properties may be developed.

It is expected that wrapping membranes of drugs having different digestion and absorption may be developed.
2. In cases where it is necessary to remove phospholipids from an oil, it is expected that removal of phospholipids may be easier by changing the composition of the phospholipids.
3. In cases where an oil containing phospholipids is utilized, the following effects may be obtained by changing the composition of the phospholipids:

It is expected that oils having different physical properties (preferable viscosity, taste, touch to the tongue and the like) from those of conventional oils may be developed.

By decreasing the content of PE which is said to be a cause of browning of oils, it is expected that oils which are hardly browned may be developed.
4. By changing the composition of the phospholipids which are main components of biomembranes, it is expected that properties of biomembranes (temperature sensitivity, resistance to dryness and the like) may be changed. Further, it is expected that changing the composition of the phospholipids may influence on the metabolism of biomembranes, so that aging may be slowed or accelerated.

EXAMPLES

The present invention will now be described more concretely by way of examples. It should be noted that the present invention is not restricted to the following Examples.

Example 1

Construction of Plasmid for Transformation

Using the pBluescript plasmid (commercially available from Stratagene, the pBluescript plasmid having rice PLD gene is described in WO95/09234) containing rice PLD gene SEQ ID NO: 1 described in WO95/09234 as a template, and using a primer having Sac I and Xba I recognition sites at its ends, having the nucleotide sequence of 5'-GCAGGAGCTCTAGAGGGATGACAGGACTTC-AGTTGGT-3' (SEQ ID NO: 3) and a primer having Bam HI and Eco RI recognition sites at its ends, having the nucleotide sequence of 5'-GGGAATTCGGATCCGCTTCTG-GTTGTTCTTCAGGC-3' (SEQ ID NO: 4), PCR was performed by the conventional method using a commercially available kit. The region amplified by using these primers is the region of 1008nt to 2115nt of the nucleotide sequence shown in SEQ ID NO: 1. The PCR product containing a part (1108 bp) of the PLD gene was digested with Bam HI and Sac I, and the resultant was inserted into pBI221 plasmid (commercially available from Toyobo) from which glucuronidase gene was removed by Bam HI and Sac I. By the operation described above, a plasmid (pB35P) in which the part of the PLD gene was inserted in the antisense direction downstream of the 35S promoter was obtained.

Example 2

Introduction of Gene into Rice by Electroporation Method

Surfaces of immature seeds of Japonica rice variety "Tsukinohikari" were sterilized with 70% ethanol for 30 seconds and then with 1% sodium hypochlorite solution for 40 minutes, and the seeds were then washed three times with sterilized water. The seeds were placed on 2N6 solid medium and cultured at 30° C. in the dark. The calli dedifferentiated from the scutella of the immature seeds were subcultured to N6 liquid medium and the resultant was cultured on a rotary shaker (125 rpm) at 25° C. The cultured cells were subcultured to fresh medium every week.

The cells on the third day from the beginning of the subculture were suspended in an enzyme solution containing 1.0% Cellulase Onozuka RS (Yakult Honsha Co., Ltd.), 1.0% Macerozyme R10 (Yakult Honsha Co., Ltd.), 0.1% Pectolyase Y-23 (Seishin Seiyaku), 0.5% Dricellase (Kyowa Hakko) and 0.4 M mannitol, and the suspension was incubated at 30° C. in the dark for 3 hours. The cell suspension was then filtered through 20 μm Nylon mesh and the obtained filtrate was centrifuged at 50×g for 5 minutes. The obtained precipitate of protoplasts was suspended in 0.4 M mannitol and the protoplasts were washed twice with this solution. The obtained protoplasts were suspended in EPAA buffer (Tada Y., Sakamoto M., Fujimura T. (1990), Efficient gene introduction into rice by electroporation and analysis of transgenic plants: use of electroporation buffer lacking chloride ions. Theor.Appl.Genet. 80:475–180) to a population density of $2 \times 10^6$ cells/ml and the suspension was placed on ice for 5 minutes. To the protoplast suspension, 10 μg of pGL2 plasmid (Bilang R., Iida S., Peterhans A., Potrykus I., Paszkowski J. (1991) The 3'-terminal region of the hygromycin-B-resistance gene is important for its activity in *Escherichia coli* and *Nicotiana tabacum*. Gene 100:247–250) and 30 μg of pB35P plasmid which was linearized by Eco RI were added and electric pulse of 250 μF, 600 V/cm was applied to the suspension using an electroporation apparatus (Bio-Rad, USA). The pulse-treated protoplasts were placed on ice for 15 minutes and then at room temperature for 30 minutes. Protoplasts were collected by centrifugation and suspended in R2-1 medium containing 1.25% Seeplaque (trademark) agarose (FMC) to a cell population of $3 \times 10^5$ cells/ml. The suspension was then solidified on 9 cm petri dish in the form of small droplets. To this, R2-1 medium and rice Oc cells (Baba A, Hasezawa S, Shono K: Cultivation of rice protoplasts and their transformation mediated by Agrobacterium spheroplast. Plant Cell Physiol. 27:463–471(1986)) were added and the resultant was cultured at 25° C. in the dark.

Two weeks later, the liquid medium and Oc cells were removed and R2-t medium was added, followed by culture at 25° C. under continuous illumination. One week later, the medium was replaced with R2-t medium containing 40 mg/l hygromycin and culture was continued. One week later, the agarose droplets containing calli with diameters of about 0.2–0.5 mm were disrupted together with a small amount of sterilized water and the resultant was placed on N6-12 medium containing 40 mg/l of hygromycin, followed by culturing the resultant at 25° C. under continuous illumination. When the calli grew to have a diameter of not less than 2 mm, the calli were transplanted to N6S3 medium containing 40 mg/l of hygromycin, and culture was further continued. Differentiated plants which grew to a height of not less than about 10 cm were transplanted to pots and cultivated in a green house. The media used and references are as follows:

| Compositions of Media | |
|---|---|
| 2N6 Medium (pH 5.8) N6 Basal Medium (Chu 1978) | |
| Casamino Acid | 1000 mg/ml |
| 2,4-D | 2.0 mg/ml |
| Sucrose | 20000 mg/ml |
| Gelrite | 2000 mg/ml |
| N6 Liquid Medium (pH 5.8) N6 Basal Medium | |
| Casamino Acid | 300 mg/ml |
| 2,4-D | 1.0 mg/ml |
| Sucrose | 30000 mg/ml |
| R2-1 Medium (pH 5.8) R2 medium inorganic salts (Ohira et al. 1973) MS medium vitamins (Murashige and Skoog 1962) | |
| Casamino Acid | 1000 mg/ml |
| 2,4-D | 1.0 mg/ml |
| n-propyl gallate | 0.05 mg/ml |

-continued

| Compositions of Media | |
|---|---|
| Sucrose | 68500 mg/ml |
| Glucose | 36000 mg/ml |
| R2-medium (pH 5.8) R2 medium inorganic salts MS medium organic components | |
| Casamino Acid | 1000 mg/ml |
| 2,4-D | 1.0 mg/ml |
| Sucrose | 20000 mg/ml |
| Glucose | 10000 mg/ml |
| N6-12 Medium (pH 5.8) N6 basal medium | |
| Casamino Acid | 2000 mg/ml |
| 2,4-D | 0.2 mg/ml |
| 6-BA | 0.5 mg/ml |
| ABA | 5.0 mg/ml |
| Sucrose | 20000 mg/ml |
| D-sorbitol | 30000 mg/ml |
| Gelrite | 2000 mg/ml |
| N6S3 Medium half concentrations of N6 medium major salts N6 medium minor salts N6 medium vitamins AA medium amino acids (Toriyama and Hinata 1985) | |
| Casamino Acid | 1000 mg/ml |
| NAA | 0.2 mg/ml |
| Kinetin | 1.0 mg/ml |
| Sucrose | 20000 mg/ml |
| Gelrite | 3000 mg/ml |

References

Chu,C.-C.(1978)The N6 medium and its application to anther culture of cereal crops. In Proc. Symp. Plant Tissue Culture. Peking: Science Press, pp.43–50

Murashige, T. and Skoog, F. (1962) A revised medium for rapid growth and bio assay with tobacco tissue culture. Physiol.Plant. 15:473–497.

Ohira, K., Ojima, K. and Fujiwara, A. (1973) Studies on the nutrition of rice cell culture I. A simple, defined medium for rapid growth in suspension culture. Plant Cell Physiol. 14:1113–1121.

Toriyama, K., Hinata, K. and Sasaki, T. (1986) Haploid and diploid plant regeneration from protoplasts of anther callus in rice. Theor. Appl. Genet. 73:16–19.

Example 3

Confirmation of Introduction of Gene by Southern Analysis and Confirmation of Effects of Antisense Gene by Western Analysis DNAs were prepared from leaves of fructified 5 transformed rice and subjected to Southern analysis (Hiei Y., Ohta S., Komari T., Kumashiro T. (1994) Efficient transformation of rice (*Oryza sativa*) mediated by Agrobacterium and sequence analysis of the boundaries of the T-DNA. Plant J. 6:271–282). The DNAs were digested with Eco RI. A probe was prepared by using a cDNA fragment with a size of 984 bp obtained by digesting the pBluescript plasmid containing the PLD gene described in section 1 above by Hinc II as a template.

In the DNAs from non-transformed plants, the 8.1 kb fragment alone was detected, while in the DNAs from transformed plants, new fragments were detected for all of the transformants.

A leaf (0.2 g) of each transformant was frozen with liquid nitrogen and the resultant was powdered with a mortar, followed by extraction of soluble proteins with 0.4 ml of 50 mM Tris-HCl (pH 7.0). After centrifugation at 10,000×g, at 4° C. for 10 minutes, the supernatant was recovered and 15 μl aliquot thereof was subjected to Western analysis (Burnette W. N. (1981) Western blotting: Electrophoretic transfer of proteins from sodium dodecyl sulfate-polyacrylamide gels to unmodified nitrocellulose and radiographic detection with antibody and radioiodinated protein A. Anal.Biochem. 112:195–203). The concentration of the polyacrylamide gel was 7.5%. The antibody (Ueki J., Morioka S., Komari T., Kumashiro T. (1995) Purification and characterization of phospholipase D (PLD) from rice (*Oryza sativa* L.) and cloning of cDNA for PLD from rice and maize (*Zea mays* L.) Plant Cell Physiol. 36:903–914) was reacted at a concentration of 8.9 μg/ml IgG.

Among the transformants, in one individual (hereinafter also referred to as "SAP8"), PLD protein was not detected, so that the effect by the antisense gene was observed. In the Southern analysis of SAP8, in addition to the 8.1 kb fragment, two larger fragments were detected.

Example 4

Preparation of Suspension of Cultured Cells Originated from Immature Embryo of Seeds of Transformed Rice Sixteen seeds fructified in the transformed rice (SAP8) were randomly selected and a suspension of cultured cells originated from each of the immature embryos of the seeds was prepared. In accordance with the method described in Example 2, the suspension cultures were subcultured to fresh N6 liquid medium every week.

Proteins were extracted from the cultured cells at the 6th day from the beginning of the subculture by the method described in Example 3, and Western analysis was performed on the extracted protein. As a result, there were cultured cells in which PLD was detected and cultured cells in which PLD was not detected, and the ratio of these types of cells was 1:3. In the cultured cells in which PLD was detected, only the 8.1 kb fragment was detected, while in the cultured cells in which PLD was not detected, in addition to the 8.1 kb fragment, two larger fragments were detected. These results indicate that the introduced genes are two copies which exist in loci close to each other, and that the gene was segregated in the next generation of SAP8. No differences in the proliferation rate and outer appearance were observed between the cultured cells in which PLD was detected and the cultured cells in which PLD was not detected.

Example 5

Extraction of Phospholipids and Analysis of Composition Thereof

In accordance with the method described in a reference (Satou N., Okuyama H. (1987) Analysis of plant membrane lipids. Proteins, Nucleic Acids and Enzymes, Extra Edition, No.30:163–170), the cultured cells (0.5 g) on the 6th day from the beginning of the subculture was placed in a polypropylene tube with an inner volume of 1.5 ml and the tube was tightly closed. The tube was heat-treated by immersing the tube in boiling water for 5 minutes and then lipids were extracted with a solvent. The solvent was evaporated from the recovered lipids and the lipids were dissolved in 0.5 ml of chloroform:methanol (2:1). On a Silica Gel 60 Chromatography Plate (Merck) for thin layer chromatography, 20 μl aliquot of the solution was spotted and the spot was developed with chloroform:methanol:acetic acid:water (25:15:4:2). Ninhydrin (commercially available from Wako Pure Chemical Industries, Ltd.) was sprayed to the dried plate and the resulting plate was heated at 120° C. for 5 minutes. Based on the mobilities of the standard phospholipids included in a kit (commercially available from Funakoshi), the phospholipid of each spot was identified. Paying attention to the phospholipids PE and PS which are detected with ninhydrin, the ratio of the amounts of PE and PS in the respective cultured cells was determined. Quantification was carried out using a densitometer (Model GS-670, Bio Rad), and the above-mentioned standard phospholipids were used for the preparation of a calibration curve.

The ratio PS/PE was 3.5±0.2% for the cultured cells in which PLD was detected, while the ratio PS/PE for the cultured cells in which PLD was not detected was 5.3±0.3%. These results indicate that the relative ratio of the amount of PS to the amount of PE was changed in the cultured cells by the introduction of the antisense gene.

What is claimed is:

1. A method for changing composition of phospholipids produced by a host plant cell, comprising transforming said host plant cell with a recombinant DNA having an antisense gene of phospholipase D gene, which antisense gene is expressed in said host plant cell to produce a mRNA that hybridizes with mRNA of phospholipase D gene in said plant cell thereby inhibiting expression of said phospholipase D gene.

2. The method according to claim 1, wherein said plant cell is a cell of a spermatophyte.

3. The method according to claim 2, wherein said cell of the spermatophyte is a cell of a monocotyledon.

4. The method according to claim 3, wherein said cell of the monocotyledon is a rice cell.

5. The method according to anyone of claims 1 or 2–4, wherein said antisense gene of phospholipase D gene is an antisense gene of a native phospholipase D gene of the host plant cell.

* * * * *